United States Patent [19]

Fujiwara et al.

[11] Patent Number: 4,868,290
[45] Date of Patent: Sep. 19, 1989

[54] 4'-DEOXY-3''-DEMETHOXY-3''-METHYLENEDESMYCOSIN DERIVATIVES AND SYNTHETIC INTERMEDIATES THEREOF

[75] Inventors: Tatsuro Fujiwara; Tomoko Yashiro; Hideo Sakakibara, all of Shizuoka, Japan

[73] Assignee: Toyo Jozo Kabushiki Kaisha, Shizuoka, Japan

[21] Appl. No.: 125,155

[22] Filed: Nov. 25, 1987

[51] Int. Cl.$^4$ .................................. C07H 17/08
[52] U.S. Cl. ........................................... 336/7.1
[58] Field of Search .................................. 536/7.1

[56] References Cited

U.S. PATENT DOCUMENTS

| | | | |
|---|---|---|---|
| 4,345,069 | 8/1982 | Sakakibara et al. | 536/7.1 |
| 4,415,730 | 11/1983 | Fujiwara et al. | 536/7.1 |
| 4,421,911 | 12/1983 | Fujiwara et al. | 536/7.1 |
| 4,652,638 | 3/1987 | Fujiwara et al. | 536/7.1 |

FOREIGN PATENT DOCUMENTS 86-194765  11/1984  Japan.

OTHER PUBLICATIONS

"Novel Semisynthetic Oxo and Alkyl Macrolide Antibacterials and Related Derivatives", *Journal of Chemical Society*, Perkins Transactions I, No. 6, Jun. 1988, by A. Fishman et al., pp. 1189–1209.

*Chemical Abstracts*, vol. 105, No. 19, No. 172991b, Nov. 1986, p. 795.

*Chemical Abstracts*, vol. 107, No. 19, No. 176412c, Nov. 1987, p. 765.

*Primary Examiner*—Johnnie R. Brown
*Assistant Examiner*—Elli Peselev
*Attorney, Agent, or Firm*—Young & Thompson

[57] ABSTRACT

4''-deoxy-3''-demethoxy-3''-methylene-desmycosin derivatives of the formula

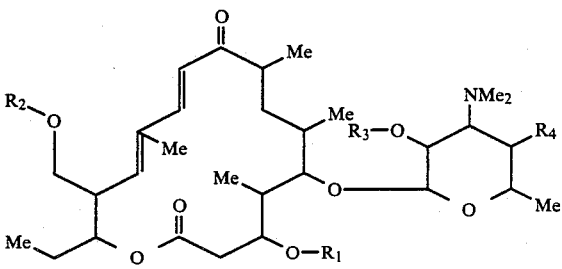

wherein
R$_1$ is hydrogen, acyl or substituted carbamoyl,
R$_2$ is

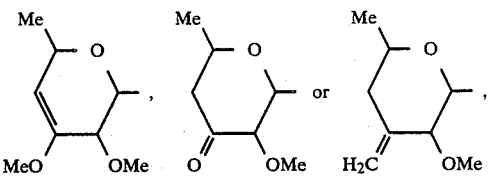

R$_3$ is hydrogen or a protective group for hydroxy, R$_4$ is hydrogen, hydroxy or protected hydroxy, and Me is —CH$_3$, and pharmaceutically acceptable salts thereof are produced.

These novel derivatives have antibiotic properties superior to the known related antibiotics tylosin and desmycosin.

6 Claims, No Drawings

4'-DEOXY-3"-DEMETHOXY-3"-METHYLENEDE-SMYCOSIN DERIVATIVES AND SYNTHETIC INTERMEDIATES THEREOF

This invention relates to novel 4"-deoxy-3"-demethoxy-3"-methylene-16 membered macrolide antibiotic derivatives.

Processes for the synthesis of 16 membered macrolide antibiotics having a mycinose moiety, such as tylosin, are well known. According to these processes, the mycinose moiety is usually modified at its 4 position, for example 4"-deoxy- or 4',4"-di-deoxy-desmycosin derivatives (Japan. Patent Unexam. Publ. No. 57-154197), 3-O-acyl-4"-deoxy-desmycosin derivatives (Japan. Patent Unexam. Publ. No. 59-141596), 4"-deoxy- or 4',4"-di-deoxy-19-deformyldesmycosin derivatives (Japan. Patent Unexam. Publ. No. 59-13596 and No. 59-121299) and 20-deoxo-20-acylmethylene-4"-deoxy-desmycosin derivatives (Japan. Patent Unexam. Publ. No. 61-129195). However, no compounds wherein methylene is introduced at the 3" position have been reported.

Compounds other than tylosine, having superior antimicrobial and antibacterial activity are useful for therapeutic treatment and the search for such novel derivatives is thus very important. However, no compound in which methylene is introduced at the 3" position of the mycinose moiety of tylosin derivatives have been reported.

Against this background, we have prepared compounds according to the present invention by modifying the 3" position of desmycosin derivatives, investigated their antimicrobial activity, and found that 19-deformyl desmycosin derivatives of the formula (1) hereinbelow have superior Antimicrobial activities as compared with desmycosin.

An object of the present invention is thus to provide compounds of the formula

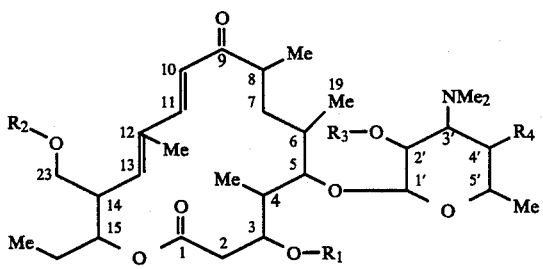

(1)

wherein
R₁ is hydrogen, acyl or substituted carbamoyl,
R₂ is

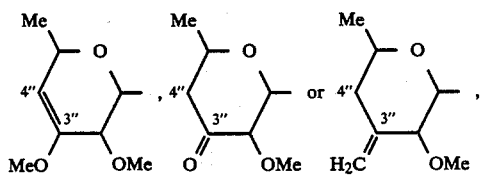

R₃ is hydrogen or a protective group for hydroxy,
R₄ is hydrogen, hydroxy or protected hydroxy, and
Me is -CH₃; or salts thereof.

More particularly, the object of the present invention is to provide compounds of the formula:

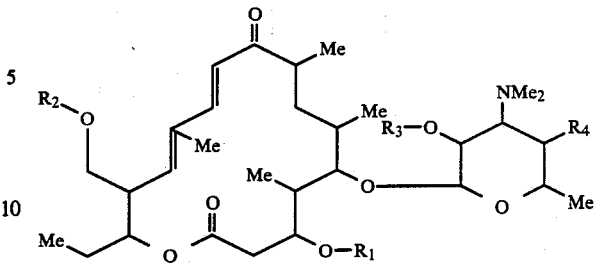

wherein
R₁ is hydrogen, acyl or

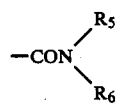

where
R₅ is lower alkyl, phenyl, phenyl C-C₃ lower alkyl, or phenyl substituted by alkyl of C₁-C₂, R₆ is hydrogen or lower alkyl, R₂ is

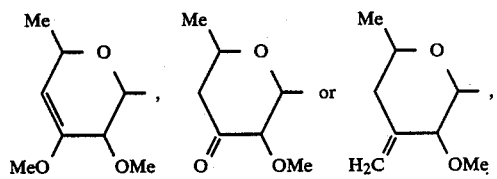

R₃ is hydrogen, C₁-C₄ lower alkanoyl or halogenated acetyl, R₄ is hydrogen, hydroxy, C₁-C₄ lower alkanoyloxy or halogenated acetoxy, and Me is CH₃; and pharmaceutically acceptable salts thereof.

The term salt as used herein means a pharmacologically acceptable salt. Examples of such salts are inorganic salts such as hydrochloride, sulfate or phosphate, and organic salts such as acetate, propionate, tartrate, citrate, succinate, malate, aspartate or glutamate. Other non-toxic salts can be included.

The process for production of the compounds (1) according to the present invention is illustrated below. In this process the formula (1) minus the substituents at the 3, 2' and 4' positions and minus the mycinose moiety, i.e. the formula

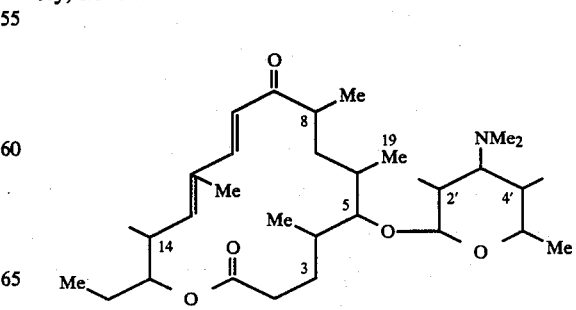

will be represented schematically as

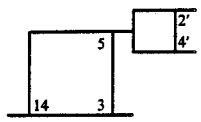

wherein each number in the figure represents a position at which a substituent may be attached.

A compound (1) of the present invention can be prepared, for example, according to the reaction scheme illustrated below, from 19-deformyl desmycosin or 19deformyl-4'-deoxydesmycosin.

In the production of the compound (1), the production process, i.e. steps (1a)-(11) below, can be traced by silica-gel thin layer chromatography (TLC) or high performance liquid chromatography (HPLC) and the reaction can be terminated upon determination of maximum concentration of the generated compound.

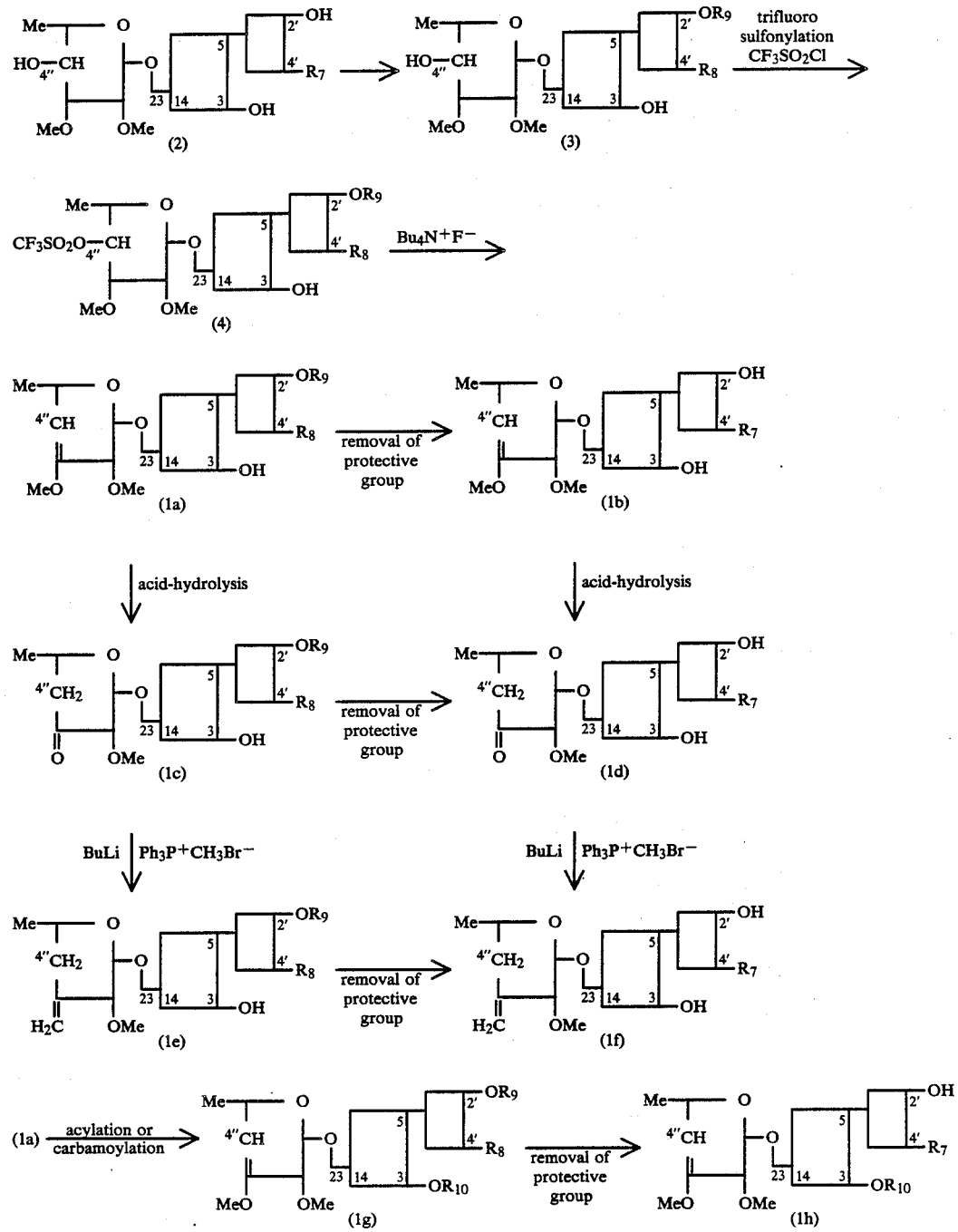

-continued

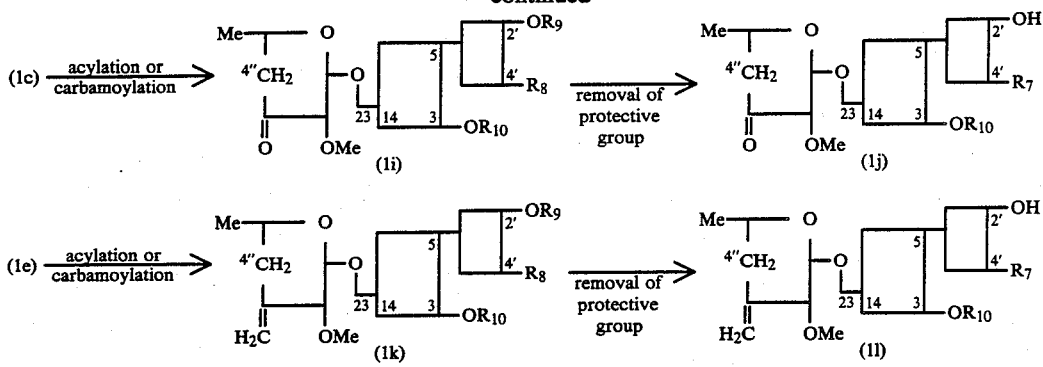

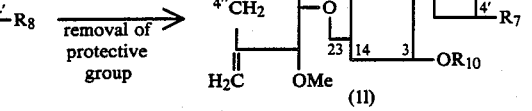

R5, R6; same as before
R7; H or OH
R8; H or —OR9      R5
R9; protective group for hydroxy
R10; acyl or —CON
Me; methyl                \
Ph; phenyl                 R6
Bu; butyl The above starting compound (2) is known, i.e. 19deformyldesmycosin was disclosed in Japan. Patent Unexam. Publ. No. 56-55399 and 19-deformyl-4′-deoxydesmycosin was disclosed in Japan. Patent Unexam. Publ. No. 58-13596. The hydroxy group at position-2′ and optionally at -4′ (when R7 is hydroxy), in the starting compound (2) is previously protected before starting the reaction and the protective group is thereafter removed.

A known protective group which can be easily removed after completion of the reaction is, for example, lower alkanoyl such as acetyl, propionyl or butyryl or halogenated acetyl such as chloroacetyl, dichloroacetyl, trichloroacetyl or trifluoroacetyl. Among these, acetyl is preferred.

Introduction of acetyl can be performed by reacting the above compound (2) with acetic anhydride in an inert organic solvent. Examples of inert organic solvent are dichloromethane, chloroform, dichloroethane, acetone and acetonitrile. The preferred reaction temperature is room temperature or below. Isolation of the product (3) can be performed by known methods, such as a process disclosed in Japan. Patent Unexam. Publ. No. 58-13596 and No. 58-121299.

A method for obtaining a product (4) by trifluoromethane sulfonylation of hydroxy at the 4″ position in compound (3) can be performed by a known process such as that disclosed in the same publications No. 58-13596 and No. 58-121299 mentioned above.

A 3″,4″-dehydroxylation of the mycinose moiety in compound (4) can be performed by reaction with tetrabutylammonium fluoride in an organic solvent. The preferred organic solvent is tetrahydrofuran. The amount of tetrabutylammonium fluoride is preferably equimolar or a slight molar excess. Reaction proceeds at room temperature or slightly elevated temperature. Isolation of the product (1a) can be performed by distilling off the reaction solvent, pouring the residue into aqueous alkali such as aqueous ammonium, extracting the resultant mixture with water immiscible organic solvent such as chloroform and driving off the solvent.

Removal of the protective group for R9, i.e. protective group for hydroxy at position-2′ and -4′, or protective group for hydroxyl at position-2′, in product (1a) can be easily performed by known processes. For example, acetyl can be removed by treatment in methanol under heating to obtain the product (1b).

As a next step, the corresponding 3″-demethoxy3″oxo-compound can be prepared from compound (1a) by hydrolyzing the compound (1a) under acidic conditions, for example in an aqueous solvent which may contain watermiscible organic solvent such as acetonitrile, in the presence of acid such as hydrochloric acid or trifluoroacetic acid. Reaction proceeds under ice-cooling. Isolation of the product (1c) can be effected by adjusting the reaction mixture of pH 9-10 by adding aqueous alkali and extracting with water-immiscible organic solvent such as chloroform.

In the above reaction a compound (1a) can be replaced by a compound (1b) and the product (1d) can thus be obtained.

The corresponding 3″-methylene compound (1e) can be prepared from a compound (1c) by reacting the compound (1c) with methylene triphenylphosphoran solution in an inert organic solvent such as tetrahydrofuran. Methylene triphenylphosphoran solution is prepared by pouring methyltriphenylphosphonium bromide (Ph3P+CH3Br-) into dry tetrahydrofuran and adding butyl lithium (BuLi) dissolved in organic solvent such as hexane under a stream of inert gas such as argon.

Reaction of a compound (1c) with methylene triphenylphosphoran can proceed under ice-cooling. Methylene triphenylphosphoran is used in a molar excess relative to compound (1c), and is generally 3-4 times molar excess. 3″methyleneation preferably proceeds under an atmosphere of inert gas such as argon. Isolation of the product (1e) from the reaction mixture can be effected by adding dilute acid to stop the reaction, adjusting the reaction mixture to pH 9-10 with addition of aqueous alkali such as ammonia and extracting the mixture with water-immiscible organic solvent such as chloroform.

As for preparation reaction of the corresponding 3″-methylene compound, the compound (1c) can be replaced by a compound (1d), and the product (1f) can thus be obtained. A protective group R9 in compound (1e) can be removed by the same removing process as used for compound (1a), and the product (1f) is thus obtained.

The next reaction process, namely acylation or substituted carbamoylation of hydroxy at position-3', can proceed by acylating or carbamoylating the compound (1a), (1c) or (1e), and the product (1g), (1i) or (1k), respectively, is produced.

The acylation reaction can proceed by reacting the compound (1a), (1c) or (1e) with a carboxylic acid of the formula $$R_{11}-COOH \quad (5)$$

wherein $R_{11}$ is lower alkyl, substituted or non-substituted phenyl, substituted or non-substituted phenyl-lower alkyl or heterocyclic lower alkyl, or its reactive derivatives as an acylating agent. That is, the acyl component may comprise lower alkanoyl, substituted or non-substituted benzoyl, substituted or non-substituted phenyl-lower alkanoyl or thienylacetyl.

Examples of carboxylic acid (5) are lower fatty acid such as acetic acid, propionic acid, butyric acid, isobutyric acid, valeric acid, substituted or non-substituted benzoic acid such as benzoic acid, substituted or non-substituted phenyl-lower fatty acid such as phenylacetic acid, 2-phenylpropionic acid, 3-phenylpropionic acid, 2phenylbutyric acid or 2-phenylisovaleric acid, or heterocyclic-lower fatty acid such as thienylacetic acid. The benzene ring in the above benzoic acid and phenyl-lower fatty acid can optionally be substituted by preferred substituents such as 1-3 lower alkyl, lower alkoxy or halogen.

The reactive derivatives in the above reaction are acylating reagents for hydroxy that are commonly used in the organic chemistry. For example, acid halides such as acid bromide or acid chloride, acid anhydride, mixed anhydride, active ester or acid azide can be mentioned.

Carboxylic acid (5) can also be provided by using N,N'-carbonyl-bis-imidazole or iso-oxazolium salt together with a known condensation reagent, for example a diimide such as N,N'-di-cyclohexylcarbodiimide (DCC) or N-cyclohexyl-N'-2-(morphoryl-4)-ethylcarbodiimide.

The acylating reaction generally proceeds in an organic solvent. Examples of preferred organic solvents are acetone, tetrahydrofuran, dioxane, dimethylformamide, dimethylacetamide, chloroform, dichloromethane or pyridine. If an acid is generated in the acylating reaction, there is preferably added a tertiary organic amine such as triethylamine, pyridine, picolin, collidine, quinoline, isoquinoline, N-methylpiperidine, N-methylmorpholine, dimethylaniline, dimethylaminopyridine or tribenzylamine. The acylating reaction proceeds at room temperature or an elevated temperature of at most 50-60° C.

Isolation of the product (1g), (1i) or (1k) wherein $R_{10}$ is acyl can be performed by adding water to the reaction mixture and extracting with water-immiscible organic solvent such as chloroform, dichloroethane methylisobutyl ketone, ethyl acetate or butyl acetate under an alkaline pH of 8-10.

The protective group $R_9$ in the compound (1g), (1i) or (1k) wherein $R_{10}$ is acyl, is removed by the same process as for removal of the protective group in the compound (1a), and the compound (1g), (1i) or (1k) wherein $R_{10}$ is acyl can thus be obtained.

The above carbamoylation reaction can proceed by reacting the product (1a), (1c) or (1e) with N,N'-carbonyldiimidazole in an inert organic solvent and reacting the thus-obtained imidazolide compound, which may optionally be isolated from the reaction mixture, with an amine of the formula

(6)

wherein $R_5$ and $R_6$ have the same meanings as before.

The imidazolide compound can be isolated by pouring the reaction mixture into water, extracting the resultant aqueous layer with water-immiscible organic solvent such as chloroform under weakly acidic conditions and removing the organic solvent therefrom.

Examples of the above amine (6) are mono-lower alkylamine such as methylamine, ethylamine, propylamine and butylamine, di-lower alkylamine such as dimethylamine, diethylamine, dipropylamine, methyl ethylamine, methyl propylamine and ethlyl propylamine, phenylamine which may optionally be substituted, such as aniline, o-(m- or p-) toluidine, o-(m- or p-)xylidine, o-(m- or p-)anisidine, o-(m- or p-)chloroaniline, o-(m- or p-)fluoroaniline, or 2,3,-(2,4,-, 2,5-, 2,6-, 3,4- or 3,5-)dichloroaniline, N-lower alkyl-phenyl, in which phenyl may optionally be substituted, such as N-methylaniline, phenyl-lower alkylamine, which may optionally be substituted, such as benzylamine, β-phenylethylamine, α-methylbenzylamine or β-phenylpropylamine, or N-lower alkyl-phenyl-lower alkylamine, in which phenyl may optionally be substituted, such as N-methylbenzylamine.

The above reaction with imidazolide compound and amine (6) can be performed in an inert organic solvent under heating, however in the case where reaction proceeds at room temperature heating is not required. Examples of inert organic solvent are dichloroethane, benzene, toluene and dioxane.

Isolation of the product (1g), (1i) or (1k) wherein $R_{10}$ is substituted carbamoyl can be performed by the same procedure as for isolation of the compound wherein $R_{10}$ is acyl.

The protective group R9 in the compound (1g), (1i) or (1k) wherein $R_{10}$ is substituted carbamoyl, is removed by the same process as for removal of the protective group in the compound (1a). The compound (1h), (1j) or (1l) wherein $R_{10}$ is substituted carbamoyl can thus be obtained.

The thus-obtained compound (1), i.e. compound (1a)-(1l), can be purified if required at any process step or after the final step. For example, the product can be purified by column chromatography using silica-gel, activated alumina or adsorption resin by eluting with suitable solvent such as benzene-acetone or chloroform-methanol.

The minimum inhibitory concentration (MIC) of compounds (1) according to the present invention is illustrated in Table 1.

Compounds of the present invention may include but are not limited to the following:
4''-deoxy-3'',4''-di-dehydro-19-deformyldesmycosin,
4''-deoxy-3''-demethoxy-3''-oxo-19-deformyldesmycosin,
4''-deoxy-3''-demethoxy-3''-methylene-19-deformyldesmycosin,
4''-deoxy-3''-demethoxy-3''-methylene-3-0-dimethylcarbamoyl-19-deformyldesmycosin, 4"-deoxy-3"-demethoxy-3"-methylene-3-0-propionyl-19-deformyldesmycosin,
and a pharmaceutically acceptable salt thereof.

Additional compounds of the present invention are disclosed in the following examples.

The compound numbers designated in Table 1 are defined as follows:

| | |
|---|---|
| Compound 1: | 4"-deoxy-3"-demethoxy-3"-oxo-19-deformyldesmycosin; |
| Compound 2: | 4',4"-dideoxy-3",4"-di-dehydro-19-deformyldesmycosin; |
| Compound 3: | 4"-deoxy-3"-demethoxy-3"-methylene-19-deformyldesmycosin; |
| Compound 4: | 4',4"-di-deoxy-3"-demethoxy-3"-methylene-19-deformyldesmycosin; |
| Compound 5: | 4"-deoxy-3"-demethoxy-3"-methylenen-3-0-propionyl-19-deformyldesmycosin; |
| Compound 6: | 4"-deoxy-3"-demethoxy-3"-methylene-3-0-dimethylcarbamoyl-19-deformyldesmycosin, |
| Des: | Desmycosin (4'-demycarosyltylosin). |

TABLE 1

| | MIC (µg/ml) | | | | | | |
|---|---|---|---|---|---|---|---|
| | Compound | | | | | | |
| Test organisms | Compound 1 | Compound 2 | Compound 3 | Compound 4 | Compound 5 | Compound 6 | Des |
| Staph. aureus ATCC6538P | 0.39 | 0.2 | 0.39 | 0.1 | 0.39 | 0.39 | 0.78 |
| Staph. aureus MS353 | 0.39 | 0.2 | 0.39 | 0.2 | 0.78 | 0.39 | 1.56 |
| Staph. aureus MS353C36* | 0.39 | 0.2 | 0.39 | 0.2 | 0.78 | 0.78 | 1.56 |
| Staph. aureus MS353 AO | >100 | >100 | >100 | >100 | >100 | >100 | 100 |
| Staph. aureus 0119 | >100 | >100 | >100 | >100 | >100 | >100 | >100 |
| Staph. aureus 0126 | 1.56 | 6.25 | — | 0.78 | — | — | 1.56 |
| Staph. aureus 0127 | >100 | >100 | >100 | 100 | >100 | >100 | >100 |
| Staph. aureus Smith | 0.78 | 0.39 | 1.56 | 0.39 | 0.78 | 1.56 | 1.56 |
| Strept. pyogenes N.Y.5 | 0.2 | 0.2 | 0.78 | 0.1 | 0.78 | 0.78 | 0.1 |
| Strept. pyogenes 1022 | 50 | >100 | 50 | 3.13 | 100 | >100 | >100 |
| Strept. agalactiae 1020 | 0.39 | 0.39 | 0.1 | ≦0.05 | 0.2 | 0.2 | 0.2 |
| Enterococcus faecalis 1501 | 1.56 | 1.56 | 0.78 | 0.39 | 1.56 | 0.78 | 0.78 |
| Micrococcus luteus ATCC9341 | 0.2 | ≦0.05 | 0.1 | ≦0.05 | 0.2 | 0.2 | 0.2 |
| Coryne. diphtheriae P.W.8 | 0.1 | 0.2 | ≦0.05 | ≦0.05 | 0.2 | 0.1 | 0.1 |
| Bacillus subtilis ATCC6633 | 0.1 | 0.1 | 0.1 | 0.1 | ≦0.05 | 0.1 | 0.78 |
| E. coli NIHJ JC-2 | >100 | >100 | >100 | >100 | >100 | >100 | >100 |

*erythromycin resistant strain

The novel compounds according to the present invention not only have stronger antimicrobial activity against Gram-positive bacteria than does desmycosin (4'-demycarosyltylosin), but also have strong antimicrobial activity against erythromycin-resistant strains, and are thus useful as therapeutic agents for human and veterinary infectious diseases and as feed additives and growth stimulants.

The following examples illustrate the present invention.

In the examples, the silica gel used in column chromatography is, if not specified, Art 7734 silica gel, from Merck.

EXAMPLE 1

2',4'-di-0-acetyl-4"-deoxy-3",4"-di-dehydro-19-deformyldesmycosin

Tetrabutylammonium fluoride (2.2 g, 1.1 equivalent) was added to 2',4'-di-0-acetyl-4"-0-trifluoromethanesulfonyl-19-deformyldesmycosin (Japan. Patent Unexam. Publ. No. 58-13596) (6.12 g, 6.38 m mol) dissolved in tetrahydrofuran (60 ml) and the mixture was stirred at room temperature overnight and at 55° C. for 3 hours. After cooling, the reaction mixture was poured into aqueous ammonia and extracted three times with chloroform. The extract was washed with dilute aqueous ammonia and saturated sodium chloride solution, passed through Whatman 1PS filter paper and concentrated in vacuo. The residue was charged on a column of silica gel (90 g) packed with benzene and eluted with benzene-acetone (10:1) to obtain white foamy 2',4'-di-0-acetyl-4"-deoxy-3",4"-didehydro-19-deformyldesmycosin (4.33 g, yield: 83.9%).

NMR (PMX-60, CDCl$_3$, $\delta_{ppm}^{TMS}$): 1.78 (s, 12-Me), 2.05 (s, OAc), 2.33 (s, NMe$_2$), 3.48 (s, 2"-OMe), 3.52 (ss, 3"-OMe), 5.8 (d, H-13), 6.23 (d, H-10), 7.26 (d, H-11).

EXAMPLE 2

2',4'-di-0-acetyl-4"-deoxy-3"-demethoxy-3"-oxo-19-deformyldesmycosin

Trifluoroacetic acid (10 ml) was added to 2',4'-di-0-acetyl-4"-deoxy-3",4"-di-dehydro-19-deformyldesmycosin (4.33 g, 5.4 m mol) dissolved in a mixture of acetonitrile (50 ml) and water (40 ml) and the mixture was stirred overnight. The reaction mixture was alkalinized by adding aqueous ammonia and extracted three times with chloroform. The extract was washed with saturated sodium chloride solution, passed through Whatman 1PS filter paper and concentrated in vacuo. The residue was charged on a column of silica gel (90g) packed with benzene and eluted with benzene-acetone (15:1), (9:1) and (4:1) in that order to obtain white foamy 2',4'-di-0-acetyl-4"-deoxy-3"-demethoxy3"-oxo-19-deformyldesmycosin (2.73 g, yield: 63.6%).

NMR (PMX-60, CDCl$_3$, $\delta_{ppm}^{TMS}$): 1.80 (s, 12-Me), 2.03 (s, 12-me), 2.03 (s, OAc), 2.35 (s, NME$_2$), 3.52 (s, 2"-OMe), 5.85 (d, H-13), 6.25 (d, H-10), 7.23 (d, H-11).

EXAMPLE 3

4"-deoxy-3"-demethoxy-3"-oxo-19-deformyldesmycosin

2',4'-di-0-acetyl-4"-deoxy-3"-demethoxy-3"-oxo-19-deformyldesmycosin (2.73 g) was dissolved in methanol (30 ml) and stirred at 55° C. overnight. The reaction mixture was concentrated in vacuo. The residue was charged on a column of silica gel (45 g) packed with chloroform and eluted with chloroform-methanol (70:1), (50:1) and (30:1) in that order to obtain white foamy (4"-deoxy-3"-demethoxy-3"-oxo-19-deformyldesmycosin (1.95 g, yield: 80.1%).

NMR (FX-100, CDCl$_3$, $\delta_{ppm}^{TMS}$): 1.81 (s, 12-Me), 2.51 (s, NMe$_2$), 3.56 (s, 2"-OMe), 4.29 (d, H-1", J=7.57 Hz), 4.39 (d, H-1', J=7.57 Hz), 5.0 (br. t, H-15), 5.87 (d, H-13), 6.27 (d, H-10), 7.26 (d, H-11).

EXAMPLE 4

2'-O-acetyl-4',4"-di-deoxy-3",4"-di-dehydro-19-deformyldesmycosin

Tetrabutylammonium fluoride (1.14 g 1.1 equivalent) was added to 2'-O-acetyl-4'-deoxy-4"-O-trifluoromethanesulfonyl-19-deformyldesmycosin (3.0 g, 3.3. m mol) dissolved in tetrahydrofuran (60 ml) and the mixture was stirred at room temperature overnight and at 55° C. for 3 hours. After cooling, the reaction mixture was poured into aqueous ammonia and extracted three times with chloroform. The extract was washed with dilute aqueous ammonia and saturated sodium chloride solution, passed through Whatman 1PS filter paper and concentrated in vacuo. The residue was charged on a column of silica gel (50 g) packed with benzene and eluted with benzene-acetone (20:1) and (10:1) to obtain white foamy 2'-O-acetyl-4',4"-di-deoxy-3",4"-di-dehydro-19-deformyldesmycosin (2.06 g, yield: 83.9%).

NMR (PMX-60, CDCl$_3$, $\delta_{ppm}^{TMS}$): 1.78 (s, 12-Me), 2.03 (s, OAc), 2.25 (s, NMe$_2$), 3.45 (s, 2"-OMe), 3.52 (s, 3"-OMe), 4.27 (d, H-1'), 4.58 (d, H-1"), 4.6 (d, H-4"), 5.8 (d, H-13), 6.25 (d, H-10), 7.3 (d, H-11).

EXAMPLE 5

2'-O-acetyl-4',4"-di-deoxy-3"-demethoxy-3"-oxo-19-deformyldesmycosin

Trifluoroacetic acid (5 ml) was added to 2'-O-acetyl-4',4"-di-deoxy-3",4"-di-dehydro-19-deformyldesmycosin (2.06 g, 2.74 m mol) dissolved in a mixture of acetonitrile (25 ml) and water (20 ml) under ice-cooling and the mixture was stirred overnight. The reaction mixture was alkalinized by adding aqueous ammonia and extracted three times with chloroform. The extract was washed with saturated sodium chloride solution, passed through Whatman 1PS filter paper and concentrated in vacuo. The residue was charged on a column of silica gel (45 g) packed with benzene and eluted by benzene-acetone (5:1) and (3:1) in that order to obtain white foamy 2'-O-acetyl-4',4"-di-deoxy-3"-demethoxy-3"-oxo-19-deformyldesmycosin (1.08 g, yield: 32.7%).

NMR (PMX-60, CDCl$_3$, $\delta_{ppm}^{TMS}$): 1.80 (s, 12-Me), 2.05 (s, OAc), 2.23 (s, NMe$_2$), 3.53 (s, 2"-OMe), 5.83 (d, H-13), 6.25 (d, H-10), 7.26 (d, H-11).

EXAMPLE 6

4',4'-di-deoxy-3",4"-di-dehydro-19-deformyldesmycosin

2'-O-acetyl-4',4"-di-deoxy-3",4"-di-dehydro-19-deformyldesmycosin (250 mg) was dissolved in methanol (5 ml) and the mixture was stirred at 55° C. overnight. The reaction mixture was concentrated in vacuo. The residue was charged on a column of silica gel (7 g, Merck, Art 9385) packed with chloroform and eluted with chloroform-methanol (60:1) and (40:1) in that order to obtain white foamy 4',4"-di-deoxy3",4"-di-dehydro-19-deformyldesmycosin (180 mg, yield: 76.9%).

NMR (FX-100, CDCl$_3$, $\delta_{ppm}^{TMS}$): 1.79 (s, 12-Me), 2.27 (s, NM$_2$), 3.57 (s, 2"-OMe), 4.24 (d, H-1'), 4.58 (d, H-1"), 4.96 (br. t, H-15), 5.85 (d, H-13), 6.30 (d, H-10), 7.29 (d, H-11).

EXAMPLE 7

4',4"-di-deoxy-3"-demethoxy-3"-oxo-19-deformyldesmycosin

2'-O-acetyl-4',4"-di-deoxy-3"-demethoxy-3"-oxo-19-deformyldesmycosin (150 mg) was dissolved in methanol (2 ml) and the mixture was stirred at 55° C. overnight. The reaction mixture was concentrated in vacuo. The residue was charged on a column of silica gel (6 g) packed with chloroform and eluted with chloroform-methanol (50:1) and 40:1) in that order to obtain white foamy 4',4"-di-deoxy-3"-demethoxy-3"-oxo-19-deformyldesmycosin (117 mg, yield: 84.2%).

NMR (FX-100, CDCl$_3$, $\delta_{ppm}^{TMS}$): 1.80 (s, 12-Me), 2.28 (s, NMe$_2$), 3.56 (s, 2"-OMe), 4.24 (d, H-1', J=7.32 Hz), 4.39 (d, H 1", J=7.57 Hz), 4.94 (br. t, H-15), 5.85 (d, H-13), 6.32 (d, H-10), 7.30 (d, H-11)

MS (CI, isoBu, m/z): 696 (MH$^+$).

EXAMPLE 8

4"-deoxy-3"-demethoxy-3"-methylene-19-deformyldesmycosin 3 ml of a hexane solution of butyl lithium (1.5 M, 4.0 eq.) was added dropwise under an argon gas atmosphere to methyl triphenylphosphonium bromide (1.61 g, 4.0 equivalents) suspended in dry tetrahydrofuran (16 ml) and the resultant mixture was stirred at room temperature for 25 mins. to prepare a methylene triphenylphosphoran solution.

The said methylene triphenylphosphoran solution was added dropwise under an argon gas atmosphere to 800 mg (1.13 m mol) 4"-deoxy-3"-demethoxy-3"-oxo-19-deformyldesmycosin dissolved in dry tetrahydrofuran (8 ml) under ice-cooling and the mixture was stirred for 1.5 hours; whereafter 0.3 N-HCl was added thereto. The reaction mixture was left at room temperature, alkalized by adding aqueous ammonia and extracted with chloroform. The extract was washed with saturated sodium chloride solution, passed through Whatman 1PS filter paper and concentrated in vacuo. The residue was charged on a column of silica gel (20 g) packed with chloroform and eluted with chloroform-methanol (150:1), (100:1), (70:1) and (50:1) in that order to obtain white foamy 4"-deoxy-3"-demethoxy-3"-methylene-19-deformyldesmycosin (190 mg).

NMR (FX-100, CDCl$_3$, $\delta_{ppm}^{TMS}$): 1.80 (s, 12-Me), 2.51 (s, NMe$_2$), 3.52 (s, 2"-OMe), 4.12 (d, H-1", J=7.57 Hz), 4.29 (d, H-1', J=7.32 Hz), 4.90 and 5.11 (each br. s, 3"-methylene), around 5.0 (br. t, H-15), 5.86 (d, H-13), 6.26 (d, H-10), 7.27 (d, H-11);

MS (CI, isoBu, m/z): 710 (MH$^+$).

EXAMPLE 9

4',4"-di-deoxy-3"-demethoxy-3"-methylene-19-deformyldesmycosin 0.5 ml of a hexane solution of butyl lithium (1.5 M, 2.5 eq.) was added dropwise under an argon gas atmosphere to methyl triphenylphosphonium bromide (268 mg, 2.5 equivalents) suspended in dry tetrahydrofuran (4 ml) and the resultant mixture was stirred at room temperature for 10 mins. to prepare a methylene triphenylphosphoran solution.

The said methylene triphenylphosphoran solution was added dropwise under an argon gas atmosphere to 2'-0-acetyl-4'-4''-di-deoxy-3''-demethoxy-3''-oxo-19-deformyldesmycosin (220) mg, 0.33 m mol) dissolved in dry tetrahydrofuran (2 ml) under ice-cooling and the resultant mixture was stirred for 1 hour, whereafter 0.3 N-HCl was added thereto. The reaction mixture was let stand at room temperature, alkalized by adding aqueous ammonia and extracted with chloroform. The extract was washed with saturated sodium chloride solution, passed through Whatman 1PS filter paper and concentrated in vacuo. The residue was charged on a column of silica gel (10 g) packed with benzene and eluted with benzene-acetone (9:1), (7:1) and (3:1) in that order to obtain white foamy 2'-0-acetyl-4'',4''-di-deoxy-3''-demethoxy-3''-methylene-19-deformyldesmycosin (107 mg), which was thereafter dissolved in methanol (2 ml) and stirred at 55° C. overnight. The reaction mixture was concentrated in vacuo and the residue was charged on a column of silica gel (5 g) packed with chloroform and eluted with chloroform-methanol (150:1), (100:1), (70:1) and (50:1) in that order to obtain white foamy 4',4''-di-deoxy-3''-demethoxy-3''-methylene-19-deformyldesmycosin (46 mg, yield: 22%).

NMR (FX-100, CHCl$_3$, $\delta_{ppm}^{TMS}$): 1.78 (s, 12-Me), 2.29 (s,

NMe$_2$), 3.52 (s, 2''-OMe), 4.12 (d, H-1'', J=7.3 Hz), 4.29

(d, H-1', J=7.3 Hz), 4.90 and 5.11 (each br. s, 3''-methylene), around 4.95 (br. t, H-15), around 5.85 (d, H-13), 6.30 (d, H-10), 7.30 (d, H-11);

MS (CI, isoBu, m/z): 694 (MH+).

EXAMPLE 10

2',4'-di-0-acetyl-4''-deoxy-3''-demethoxy-3''-methylene-19-deformyldesmycosin

Acetic anhydride (100 μl, 4 eq.) was added to 4''-deoxy-3''-demethoxy-3''-methylene-19-deformyldesmycosin (190 mg, 0.27 m mol) dissolved in dichloromethane (2 ml) and the mixture was stirred at room temperature for 1.5 hours. The reaction mixture was diluted with chloroform (5 ml) and aqueous ammonia was added thereto to treat excess acetic anhydride. The mixture was washed with aqueous ammonia and saturated sodium chloride solution, passed through Whatman 1PS filter paper and concentrated in vacuo to obtain white foamy 2',4'-di-0-acetyl-4''-deoxy-3''-demethoxy-3''-methylene-19-deformyldesmycosin (211 mg, yield: 100%).

NMR (PMX-60, CDCl$_3$, $\delta_{ppm}^{TMS}$): 1.78 (s, 12-Me), 2.0 (s,

OAc x 2), 2.3 (s, NMe$_2$), 3.45 (s, 2''-OMe), 4.1 (d, H-1''), 4.3 (d, H-1'), 4.8 and 5.05 (each br. s, 3''-methylene), 5.85 (d, H-13), 6.25 (d, H-10), 7.3 (d, H-11).

EXAMPLE 11

2',4'-di-0-acetyl-4''-deoxy-3''-demethoxy-3''-methylene 3-0-propionyl-19-deformyldesmycosin Propionic anhydride (180 μl, 10 eq.) and 4-dimethyl-amino pyridine (3.5 mg, 0.2 eq.) were added to 2',4'-di-0-acetyl-4''-deoxy-3''-demethoxy-3''-methylene-19-deformyldesmycosin (110 mg, 0.14 m mol) dissolved in pyridine (1.5 ml) and the mixture was stirred at 55° C. for 6.5 hours. The reaction mixture was treated with aqueous ammonia and water containing sodium chloride (20 vol. excess) and filtered. The precipitate was dissolved in chloroform. The resultant solution was washed with saturated sodium chloride solution, passed through Whatman 1PS filter paper and concentrated in vacuo. The residue was charged on a column of silica gel (5 g) packed with benzene and eluted with benzene-acetone (30:1), (25:1), (20:1), (15:1), and (10:1), in that order to obtain white foamy 2',4'-di-0-acetyl-4''-deoxy-3''-demethoxy-3''-methylene-3-0-propionyl-19-deformyldesmycosin (52.4 mg).

NMR (PMX-60, CDCl$_3$, $\delta_{ppm}^{TMS}$): 1.8 (s, 12-Me), 2.05 (s,

OAc x 2), 2.3 (q, -CO-CH$_2$-), 2.35 (s, NMe$_2$), 3.45 (s, 2''-OMe), 4.1 (d, H-1''), 4.3 (d, H-1'), 4.9 and 5.05 (each br. s, 3''-methylene), 5.15 (d, H-3), 5.8 (d, H-13), 6.2 (d, H-10), 7.25 (d, H-11).

EXAMPLE 12

4''-deoxy-3''-demethoxy-3''-methylene-3-0-proprionyl-19-deformyldesmycosin:

2',4'-di-0-acetyl-4''-deoxy-3''-demethoxy-3''-methylene-3-0-proprionyl-19-deformyldesmycosin (52.4 mg) was dissolved in methanol (2 ml) and the solution was stirred at 55° C. overnight. The reaction mixture was concentrated in vacuo and the residue was charged on a column of silica gel (3.5 g) packed with chloroform and eluted with chloroformmethanol (75:1) and (30:1) in that order to obtain white foamy 4''-deoxy-3''-demethoxy-3''-methylene-3-0-propionyl-19-deformyldesmycosin (34.5 mg).

NMR (FX-100, CDCl$_3$, $\delta_{ppm}^{TMS}$): 1.81 (s, 12-Me), around 2.3 (-CO-CH$_2$-), 2.54 (s, NMe$_2$), 3.49 (s, 2''-OMe), 4.10 (d, H-1'', J=7.57 Hz), 4.18 (d, H-1', J=7.57 Hz), 4.89 and 5.09 (each br. s, 3''-methylene), around 4.95 (br. t, H-15), around 5.15 (d, H-3), around 5.9 (d, H-13), 6.21 (d, H-10), 7.33 (d, H-11);

MS (CI, isoBu, m/z): 766 (MH+).

EXAMPLE 13

2',4'-di-0-acetyl-4''-deoxy-3''-demethoxy-3''-methylene-3-0-dimethylcarbamoyl-19-deformyldesmycosin N,N'-carbonyldiimidazole (105 mg, 5 equivalent), was added to 2',4'-di-0-acetyl-4''-deoxy-3''-demethoxy-3''-methylene-19-deformyldesmycosin (100 mg, 0.13 m mol) dissolved in dichloroethane and the mixture was stirred at 55° C. overnight. The reaction mixture was poured into water, adjusted by adding dilute hydrochloric acid, and the resultant mixture was extracted three times with chloroform. The extract was washed with dilute aqueous ammonia and saturated sodium chloride solution, passed through Whatman 1PS filter paper and concentrated in vacuo. The residue was dissolved in dichloroethane, and the solute was bubbled with dimethylamine gas and stirred at room temperature for 1.5 hours. The reaction mixture was concentrated in vacuo and the residue was charged on a column of silica gel (5 g) packed with benzene and eluted with benzene-acetone (20:1), (15:1), (10:1) and (5:1) in that order to obtain white foamy 2',4'-di-0-acetyl-4''-deoxy-3''-demethoxy-3''-methylene-3-0-dimethylcarbamoyl-19-deformyldesmycosin (50.2 mg).

NMR (PMX-60, CDCl$_3$, $\delta_{ppm}^{TMS}$): 1.8 (s, 12-Me), 20.5 (s, OAc x 2) 2.35 (s, 3'-NMe$_2$), 2.9 (s, -CO-NMe$_2$), 3.45 (s, 2″-OMe), 4.1 (d, H-1″), 4.3 (d, H-1′), 4.9 and 5.05 (each br. s, 3″-methylene), 5.8 (d, H-13), 6.2 (d, H-10), 7.25 (d, H-11).

EXAMPLE 14

4″-deoxy-3″-demethoxy-3″-methylene-3-0-dimethylcarbamoyl-19-deformyldesmycosin

2′,4′-di-0-acetyl-4″-deoxy-3″-demethoxy-3″-methylene-3-0-dimethylcarbamoyl-19-deformyldesmycosin (50.2 mg) was dissolved in methanol (2 ml) and the solution was stirred at 55° C. overnight. The reaction mixture was concentrated in vacuo and the residue was charged on a column of silica gel (3.5 g) packed with chloroform and eluted with chloroform-methanol (75:1) and (30:1) in that order to obtain white foamy 4″-deoxy-3″-demethoxy-3″-methylene-3-0-methylcarbamoyl-19-deformyldesmycosin (26.4 mg).

NMR (FX-100, CDCl$_3$, $\delta_{ppm}^{TMS}$): 1.81 (s, 12-Me), 2.56 (s, 3′-NMe$_2$), 2.92 (s, -CO-NMe$^2$), 3.49 (s, 2″-OMe), 4.11 (d, H-1″, J=7.32 Hz), 4.22 (d, H-1′, J=7.08 Hz), 4.9 and 5.09 (each br. s, 3″-methylene), around 5.1 (d, H-3), around 5.9 (d, H-13), 6.14 (d, H-10), 7.34 (d, H-11); MS (CI, isoBu, m/z): 781 (MH+), 692.

EXAMPLE 15

4′,4″-di-deoxy-3″-demethoxy-3″-methylene-3-0-(thiophene-2-acetyl)-19-deformyldesmycosin Thiophene-2-acetate (1.83 g, 10 eq.) N,N′-dicyclohexylcarbodiimide (1.33 g, 5 eq.) and 4-dimethylamino pyridine (158 mg, 1 eq.) were added to 2′-0-acetyl-4″,4′-dideoxy-3″-demethoxy-3″-methylene-19-deformyldesmycosin (952 mg) dissolved in dichloromethane (25 ml) and the resultant mixture was stirred at room temperature overnight. The precipitate was filtered and the filtered liquid was washed with aqueous ammonia and saturated sodium chloride solution, passed through Whatman 1PS filter paper and concentrated in vacuo. The residue was charged on a column of silica gel (23 g) packed with benzene and eluted with benzene-acetone (20:1), (15:1) and (10:1) in that order to obtain white foamy 2′-0-acetyl-4′,4″-di-deoxy-3″-demethoxy-3″-methylene-3-0-(thiophene-2-acetyl)-19-deformyldesmycosin (733 mg), which was thereafter dissolved in methanol (7 ml), the resultant solution being stirred at 55° C. overnight. The reaction mixture was concentrated in vacuo and the residue was charged on a column of silica gel (10 g) packed with chloroform and eluted with chloroform-methanol (120:1) to obtain white foamy 4′,4″-di-deoxy-3″-demethoxy-3″-methylene-3-0-(thiophene-2-acetyl)-19-deformyldesmycosin (612 mg).

NMR (FX-100, CDCl$_3$, $\delta_{ppm}^{TMS}$): 1.80 (s, 12-Me), 2.27 (s, (NMe$_2$), 3.50 (s, 2″-OMe), 3.81 (s, -CH$_2$-thiophene), 3.97 (d, H-1′, J=7.32 Hz), 4.10 (d, H-1″, J=7.57 Hz), 4.89 and 5.11 (each br. s, 3″-methylene), 4.9 (br. t, H-15) 5.15 (d, H-3), 5.85 (d, H-13), 6.27 (d, H-10), 6.93 and 7.12 (m, thiophene), 7.34 (3, H-11);

MS (CI, isoBu, m/z): 818 (MH+).

What is claimed is:

1. A compound of the formula:

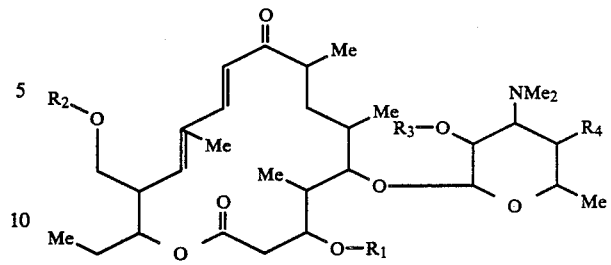

wherein
R$_1$ is hydrogen, acyl or

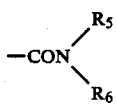

where
R$_5$ is lower alkyl, phenyl, phenyl C$_1$-C$_3$ lower alkyl, or phenyl substituted by alkyl of C$_1$-C$_2$, R$_6$ is hydrogen or lower alkyl,
R$_2$ is

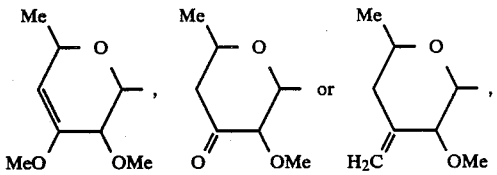

R$_3$ is hydrogen, C$_1$-C$_4$ lower alkanoyl or halogenated acetyl, R$_4$ is hydrogen, hydroxy, C$_1$-C$_4$ lower alkanoyloxy or halogenated acetoxy, and Me is CH$_3$; and pharmaceutically acceptable salts thereof.

2. A compound according to claim 1, wherein R$_3$ is hydrogen and R$_4$ is hydroxy.

3. A compound according to claim 1, wherein one of R$_3$ and R$_4$ is hydrogen.

4. A compound according to claim 1, wherein said acyl group is selected from the group consisting of lower alkanoyl, benzoyl, phenyl lower alkanoyl, thienylacetyl, or benzoyl substituted with lower alkyl, lower alkoxy or halogen.

5. A compound selected from the group consisting of:
4″-deoxy-3″,4″-di-dehydro-19-deformyldesmycosin,
4″-deoxy-3″-demethoxy-3″-oxo-19-deformyldesmycosin,
4″-deoxy-3″-demethoxy-3″-methylene-19-deformyldesmycosin,
4″-deoxy-3″-demethoxy-3″-methylene-3-0-dimethylcarbamoyl-19-deformyldesmycosin,
4″-deoxy-3″-demethoxy-3″-methylene-3-0-propionyl-19-deformyldesmycosin,
and a pharmaceutically acceptable salt thereof.

6. A compound selected from the group consisting of:
4′,4″-di-deoxy-3″,4″-di-dehydro-19-deformyldesmycosin,
4′,4″-di-deoxy-3″-demethoxy-3″-oxo-19-deformyldesmycosin,
4′,4″-di-deoxy-3″-demethoxy-3″-methylene-19-deformyldesmycosin,
4′,4″-di-deoxy-3″-demethoxy-3″-methylene-3-0(thiophene-2-acetyl)-19-deformyldesmycosin,
and a pharmaceutically acceptable salt thereof.

* * * * *